United States Patent [19]

Glover

[11] Patent Number: 5,672,804
[45] Date of Patent: Sep. 30, 1997

[54] PROCESS FOR THE REMOVAL OF POLYNUCLEAR AROMATIC COMPOUNDS FROM A VAPOR EFFLUENT FROM A NORMALLY GASEOUS HYDROCARBON DEHYDROGENATION REACTION ZONE

[75] Inventor: Bryan K. Glover, Algonquin, Ill.

[73] Assignee: UOP, Des Plaines, Ill.

[21] Appl. No.: 502,992

[22] Filed: Jul. 17, 1995

[51] Int. Cl.$^6$ ............................................. C07C 7/00
[52] U.S. Cl. ................................ 585/655; 585/807
[58] Field of Search ............................ 585/807, 655

[56] References Cited

U.S. PATENT DOCUMENTS

| | | | |
|---|---|---|---|
| 4,430,517 | 2/1984 | Imai et al. | 585/660 |
| 5,177,293 | 1/1993 | Mitariten et al. | 585/655 |
| 5,481,060 | 1/1996 | Scott et al. | 585/867 |

*Primary Examiner*—Glenn A. Caldarola
*Assistant Examiner*—In Suk Bullock
*Attorney, Agent, or Firm*—Thomas K. McBride; John G. Tolomei; John G. Cutts, Jr.

[57] ABSTRACT

A process for the removal of trace quantities of polynuclear aromatic compounds from the vapor effluent of a hydrocarbon dehydrogenation zone containing normally gaseous olefinic hydrocarbons, trace mononuclear aromatic compounds and trace polynuclear aromatic compounds by cooling the vapor effluent to condense at least a portion thereof, up to five weight percent, by introducing the resulting cooled stream into a vapor-liquid separator to produce a vapor stream containing normally gaseous olefinic hydrocarbons and having a reduced concentration of polynuclear aromatic compounds and a liquid stream containing mononuclear and polynuclear aromatic compounds and by recovering the vapor stream comprising normally gaseous olefinic hydrocarbons having a reduced concentration of polynuclear aromatic compounds.

8 Claims, 1 Drawing Sheet

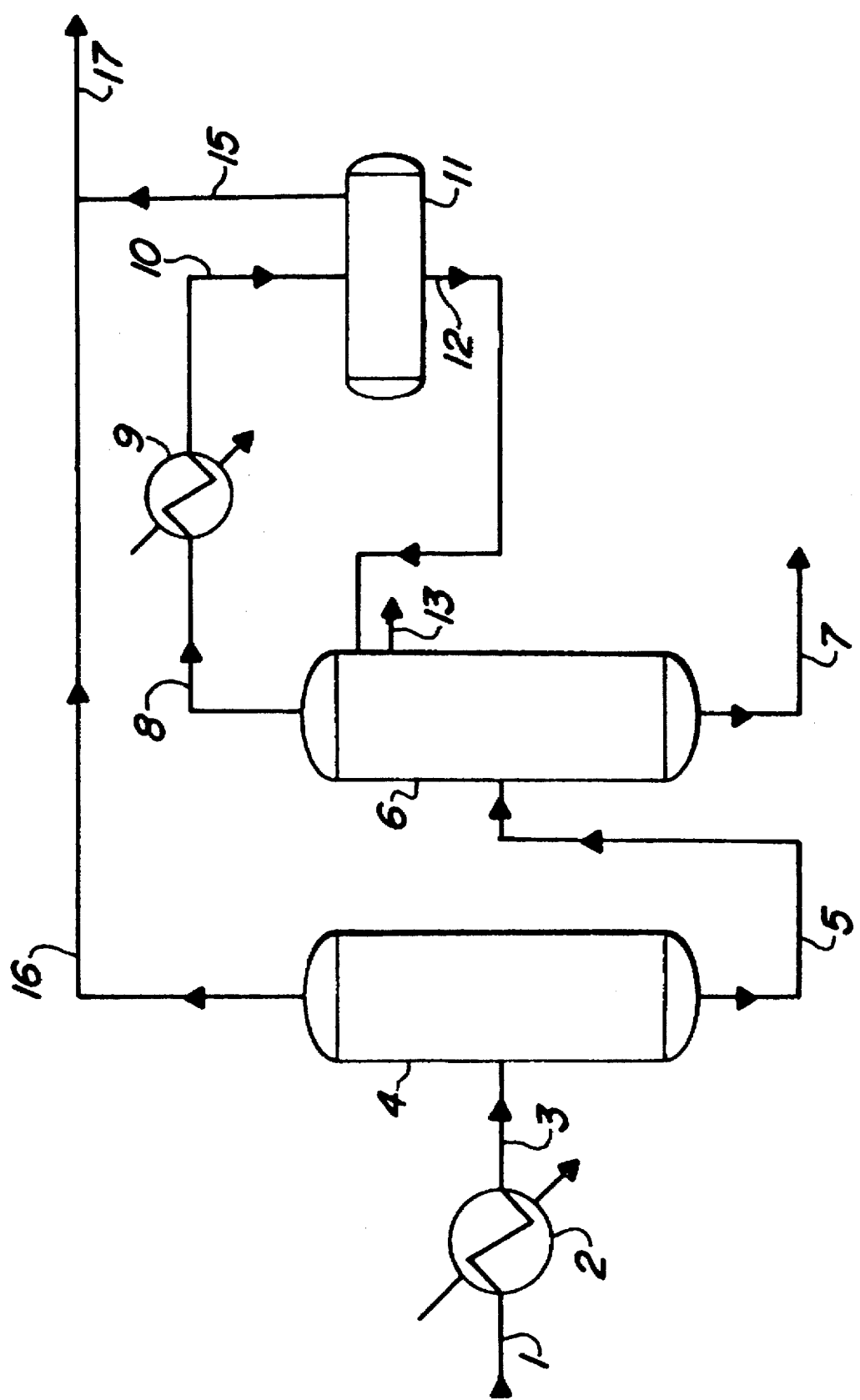

PROCESS FOR THE REMOVAL OF POLYNUCLEAR AROMATIC COMPOUNDS FROM A VAPOR EFFLUENT FROM A NORMALLY GASEOUS HYDROCARBON DEHYDROGENATION REACTION ZONE

FIELD OF THE INVENTION

The field of art to which this invention pertains is the removal and recovery of polynuclear aromatic compounds from the vapor effluent from a normally gaseous hydrocarbon dehydrogenation reaction zone.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater severity operation of existing commercial facilities has highlighted the problem which occurs in the product recovery section of hydrocarbon dehydrogenation processes. This problem is the result of the production of trace quantities of polynuclear aromatic compounds. In addition, trace quantities of mononuclear aromatic compounds are also produced and are considered to be an undesired impurity in the desired olefinic hydrocarbon product stream and must be removed. The mononuclear aromatic compounds include benzene, toluene and xylene. The polynuclear aromatic compounds are not only an undesired impurity, but also present a severe operational problem because when they condense and plate out on the cooler surfaces of the plant there are detrimental results. The deposits of polynuclear aromatic compounds are difficult to remove, they reduce the efficiency of heat exchangers and they may eventually lead to plugging.

Therefore, those skilled in the art of hydrocarbon processing have sought methods to overcome the problem posed by the production of polynuclear aromatic compounds in dehydrogenation production facilities. The process of the present invention provides a facile and economical solution to the problem of the co-production of mononuclear and polynuclear aromatic compounds in a dehydrogenation plant.

BRIEF SUMMARY OF THE INVENTION

The present invention relates to a process for the removal of trace quantities of polynuclear aromatic compounds from the vapor effluent of a hydrocarbon dehydrogenation zone containing normally gaseous olefinic hydrocarbons and trace quantities of mononuclear and polynuclear aromatic compounds.

One embodiment of the present invention may be characterized as a process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises: (a) cooling the vapor effluent to condense at least a portion thereof up to about 5 weight percent; (b) introducing the resulting cooled stream from step (a) into a vapor-liquid separator to produce a vapor stream comprising normally gaseous olefinic hydrocarbons and having a reduced concentration of polynuclear aromatic compounds and a liquid stream comprising mononuclear and polynuclear aromatic compounds; and (c) recovering the vapor stream comprising normally gaseous olefinic hydrocarbons having a reduced concentration of polynuclear aromatic compounds.

Another embodiment of the present invention may be characterized as a process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises: (a) cooling the vapor effluent to condense at least a portion thereof up to about 5 weight percent; (b) introducing the resulting cooled stream from step (a) into a vapor-liquid separator to produce a vapor stream comprising normally gaseous olefinic hydrocarbons and having a reduced concentration of polynuclear aromatic compounds and a liquid stream comprising mononuclear and polynuclear aromatic compounds; (c) separating the liquid stream comprising mononuclear and polynuclear aromatic compounds recovered in step (b) in a separation zone to produce a stream rich in mononuclear aromatic compounds; and (d) recovering the vapor stream comprising normally gaseous olefinic hydrocarbons having a reduced concentration of polynuclear aromatic compounds.

Other embodiments of the present invention encompass further details such as preferred operating conditions.

The process of the present invention provides the advantages of the removal of polynuclear aromatic compounds from a normally gaseous olefinic hydrocarbon stream and the concomitant recovery of mononuclear aromatic compounds.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the removal of trace quantities of polynuclear aromatic compounds from the vapor effluent of a hydrocarbon dehydrogenation zone. The dehydrogenation of paraffinic hydrocarbons is well known to those skilled in the art of hydrocarbon processing. Preferred paraffinic hydrocarbons used for the production of normally gaseous olefinic hydrocarbons include ethane, propane and butane.

In the dehydrogenation process, fresh hydrocarbon feed is combined with recycle hydrogen and unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream of olefinic hydrocarbons. In accordance with the present invention, the effluent from the catalytic reaction zone contains unconverted saturated hydrocarbons, olefin hydrocarbons, mononuclear aromatic compounds in an amount from about 100 to about 5,000 wppm and polynuclear aromatic compounds in an amount from about 50 to about 500 wppm. The preferred normally gaseous olefinic hydrocarbons include ethylene, propylene and butylene.

In accordance with the present invention, the dehydrogenation reaction zone effluent is preferably cooled to a temperature in the range from about 40° F. (4° C.) to about 100° F. (38° C.) to condense at least a portion thereof up to about 5 weight percent. The resulting partially condensed effluent stream is introduced into a vapor-liquid separator to produce a vapor stream containing normally gaseous olefinic hydrocarbons having a reduced concentration of polynuclear aromatic compounds and a liquid stream containing mononuclear and polynuclear aromatic compounds. The resulting liquid stream containing mononuclear and polynuclear aromatic compounds is preferably less than about 5 weight percent and more preferably less than about 3 weight percent of the vapor effluent from the hydrocarbon dehydrogenation zone and in a preferred embodiment is subsequently introduced into a separation zone to produce a stream rich in mononuclear aromatic compounds and a stream comprising polynuclear aromatic compounds. The separation zone may employ any convenient separation technique such as fractionation or adsorption, however, a fractionation zone is most preferred. Any normally gaseous hydrocarbons which may be recovered in the separation zone are returned to the vapor stream containing normally gaseous hydrocarbons. Expected mononuclear aromatic compounds are benzene, toluene and xylene.

The resulting vapor stream comprising normally gaseous olefinic hydrocarbons having a reduced concentration of polynuclear aromatic compounds, preferably less than about 1 wppm, may then be compressed, cooled, subjected to cryogenic refrigeration, treated for chloride removal, treated for water removal or fractionated, for example.

DETAILED DESCRIPTION OF THE DRAWING

With reference now to the drawing, a vapor effluent from a hydrocarbon dehydrogenation zone containing normally gaseous olefinic hydrocarbons, trace mononuclear aromatic compounds and trace polynuclear aromatic compounds is introduced into the process via conduit 1 and enters heat exchanger 2. A resulting cooled and partially condensed stream is removed from heat exchanger 2 via conduit 3 and introduced into vapor-liquid separator 4. A vapor stream containing normally gaseous olefinic hydrocarbons and having a reduced concentration of polynuclear aromatic compounds is removed from vapor-liquid separator 4 via conduits 16 and 17 and recovered. A liquid stream containing mononuclear and polynuclear aromatic compounds is removed from vapor-liquid separator 4 via conduit 5 and introduced into fractionation zone 6. A vapor stream containing mononuclear aromatic compounds is removed from fractionation zone 6 via overhead conduit 8 and cooled and partially condensed in heat exchanger 9. A cooled vapor-liquid stream from heat exchanger 9 is transported via conduit 10 and introduced into overhead receiver 11. A gaseous stream containing normally gaseous hydrocarbons is removed from overhead receiver 11 via conduits 15 and 17 and recovered. A liquid stream containing mononuclear aromatic compounds is removed from overhead receiver 11 via conduit 12 and is refluxed to fractionation zone 6. Another liquid stream containing mononuclear aromatic compounds is removed from fractionation zone 6 via conduit 13 and recovered. A liquid stream containing polynuclear aromatic compounds is removed and recovered from fractionation zone 6 via conduit 7.

The process of the present invention is further demonstrated by the following illustrative embodiment. This illustrative embodiment is, however, not presented to unduly limit the process of this invention, but to further illustrate the advantages of the hereinabove-described embodiment. The following data were not obtained by the actual performance of the present invention, but are considered prospective and reasonably illustrative of the expected performance of the invention.

ILLUSTRATIVE EMBODIMENT

An effluent from a propane-isobutane dehydrogenation zone (identified as feed) having the characteristics and flow rates presented in Table 1 is introduced into a heat-exchanger to produce a vapor and a liquid phase which are subjected to a vapor-liquid separation zone to produce a separator gas having the characteristics and flow rates presented in Table 1. A separator liquid stream having the characteristics and flow rates presented in Table 1 is recovered from the vapor-liquid separator and introduced into a fractionation zone. A fractionator bottoms stream containing essentially all of the $C_9^+$ hydrocarbon compounds is removed from the fractionation zone in an amount and having the characteristics presented in Table 1. A fractionator side-cut stream containing primarily mononuclear aromatic compounds and having the characteristics and flow rates presented in Table 1 is recovered from the fractionation zone. A fractionator gas stream having the characteristics and flow rates presented in Table 1 is removed from the fractionation zone and recovered.

TABLE 1

STREAM ANALYSIS

| Mass Flow LB/HR | Feed | Separator Liquid | Fractionator Bottoms | Fractionator Sidecut | Fractionator Gas | Separator Gas |
|---|---|---|---|---|---|---|
| $H_2$ | 8319 | 1 | | | 1 | 8318 |
| $C_1$ | 6595 | 5 | | | 5 | 6591 |
| $C_2=$ | 15 | | | | 0 | 15 |
| $C_2$ | 583 | 2 | | | 2 | 580 |
| $C_3=$ | 2348 | 26 | | | 26 | 2322 |

TABLE 1-continued

STREAM ANALYSIS

| Mass Flow LB/HR | Feed | Separator Liquid | Fractionator Bottoms | Fractionator Sidecut | Fractionator Gas | Separator Gas |
|---|---|---|---|---|---|---|
| $C_3$ | 8837 | 112 | | | 112 | 8725 |
| $IC_4=$ | 122395 | 4130 | | 5 | 4125 | 118265 |
| $IC_4$ | 139113 | 4121 | | 2 | 4119 | 134992 |
| Benzene | 24 | 7 | | 7 | | 17 |
| Toluene | 43 | 25 | 1 | 24 | | 18 |
| Xylene | 224 | 185 | 25 | 160 | | 39 |
| $C_9^+$ | 27 | 27 | 25 | 1 | | |

The foregoing description, drawing and illustrative embodiment clearly illustrate the advantages encompassed by the method of the present invention and the benefits to be afforded with the use thereof.

What is claimed:

1. A process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises:

(a) cooling substantially all of said vapor effluent to condense at least a portion thereof up to about 5 weight percent;

(b) introducing the resulting cooled stream from step (a) into a vapor-liquid separator to produce a vapor stream comprising normally gaseous olefinic hydrocarbons and having a reduced concentration of polynuclear aromatic compounds and a liquid stream comprising mononuclear and polynuclear aromatic compounds;

(c) separating said liquid stream comprising mononuclear and polynuclear aromatic compounds recovered in step (b) in a separation zone to produce a stream rich in mononuclear aromatic compounds; and (d) recovering said vapor stream comprising normally gaseous olefinic hydrocarbons having a reduced concentration of polynuclear aromatic compounds.

2. The process of claim 1 wherein said separation zone is a fractionation zone.

3. The process of claim 1 wherein said separation zone is an adsorption zone.

4. The process of claim 1 wherein said normally gaseous olefinic hydrocarbons are selected from the group consisting of ethylene, propylene and butylene.

5. The process of claim 1 wherein said mononuclear aromatic compounds are selected from the group consisting of benzene, toluene and xylene.

6. The process of claim 1 wherein the trace quantities of polynuclear aromatic compounds are present in the vapor effluent of a dehydrogenation zone in an amount from about 50 to about 500 wppm.

7. The process of claim 1 wherein the trace quantities of mononuclear aromatic compounds are present in the vapor effluent of a dehydrogenation zone in an amount from about 100 to about 5000 wppm.

8. The process of claim 1 wherein said stream comprising normally gaseous olefinic hydrocarbons having a reduced concentration of polynuclear aromatic compounds contains less than about 1 wppm polynuclear aromatic compounds.

* * * * *